(12) United States Patent
Ramamurthy et al.

(10) Patent No.: US 8,158,259 B2
(45) Date of Patent: Apr. 17, 2012

(54) SPREADING LAYER AND HUMIDITY CONTROL LAYER FOR ENHANCING SENSOR PERFORMANCE

(75) Inventors: Narayanan Ramamurthy, Alpharetta, GA (US); Huarui He, Alpharetta, GA (US); Chao Lin, Alpharetta, GA (US)

(73) Assignee: Opti Medical Systems, Roswell, GA (US)

( * ) Notice: Subject to any disclaimer, the term of this patent is extended or adjusted under 35 U.S.C. 154(b) by 1166 days.

(21) Appl. No.: 11/987,984

(22) Filed: Dec. 6, 2007

(65) Prior Publication Data

US 2008/0152864 A1    Jun. 26, 2008

Related U.S. Application Data

(60) Provisional application No. 60/869,268, filed on Dec. 8, 2006.

(51) Int. Cl.
*B32B 9/04* (2006.01)
*B32B 3/10* (2006.01)
*B05D 5/00* (2006.01)

(52) U.S. Cl. .............. 428/411.1; 427/372.2; 427/402; 428/131

(58) Field of Classification Search .......... None
See application file for complete search history.

(56) References Cited

U.S. PATENT DOCUMENTS

| | | | |
|---|---|---|---|
| 4,780,411 A | 10/1988 | Piejko et al. | |
| 4,889,797 A | 12/1989 | Amano et al. | |
| 5,788,942 A | 8/1998 | Kitani et al. | |
| 5,952,491 A * | 9/1999 | Leiner et al. | 540/467 |
| 6,211,359 B1 * | 4/2001 | He et al. | 540/469 |
| 6,613,282 B2 * | 9/2003 | Huber et al. | 422/426 |
| 2002/0068364 A1 * | 6/2002 | Arai et al. | 436/113 |

FOREIGN PATENT DOCUMENTS

| | | |
|---|---|---|
| DE | 37 17 913 A1 | 12/1987 |
| EP | 0 162 301 | 11/1985 |
| EP | 0 175 990 | 4/1986 |
| EP | 0 264 229 A | 4/1988 |
| WO | WO 93/22039 | 11/1993 |
| WO | WO 02/38257 A | 5/2002 |
| WO | WO 2006/034575 | 4/2006 |

* cited by examiner

*Primary Examiner* — Shafiqul Haq
*Assistant Examiner* — Galina Yakovleva
(74) *Attorney, Agent, or Firm* — Gilberto M. Villacorta; Steven M. Reid; Foley & Lardner LLP

(57) ABSTRACT

The invention is directed to optical sensors for measuring clinically relevant analytes, their methods of manufacture, and their various uses. In an effort to develop a dry calibration method for the optical sensors of the invention it is discovered that water content inside or in the immediate vicinity of a such a sensor can have a major impact on fluorescence intensity (i.e., a sensor's response in the dry state). Thus, one of the objectives of the invention is the elimination of the bias of sensor responses measured at different humidity environments.

12 Claims, 4 Drawing Sheets

SPREADING LAYER AND HUMIDITY CONTROL LAYER FOR ENHANCING SENSOR PERFORMANCE

This application claims the benefit of U.S. Provisional Patent Application No. 60/869,268, which was filed on Dec. 8, 2006, and is incorporated by reference in its entirety as if fully set forth herein.

FIELD OF THE INVENTION

The invention is directed to improved optical sensors for measuring clinically relevant analytes, their methods of manufacture, and their various uses. Typically, for performing an accurate measurement, a calibration step is required for eliminating sensor to sensor and instrument to instrument variations. Conventional "wet" calibration methods require that a calibration step be carried out with a calibration liquid that contains a known concentration of analyte. However, the calibration method of choice for an optical sensor to which the invention is directed is a "dry calibration" method. In a dry calibration method, fluorescence intensity of a sensor in a "dry" state (i.e., right out of the packaging) is measured. The sensor's response in the dry state is taken into account, along with the sensor's response in the "wet" state (in the present case, when in contact with a sample), to arrive at a determination of concentration of analyte in a sample, vide infra. For achieving an accurate calibration, it is essential that a calibration signal not be sensitive to variations in ambient conditions (e.g., changing levels of humidity from one measurement site to another). It has been discovered, however, that water content inside or in the immediate vicinity of a sensor can have a major impact on fluorescence intensity (i.e., a sensor's response in the dry state). Thus, one of the objectives of the invention is the elimination of the bias of sensor responses measured at different humidity environments.

ADDITIONAL BACKGROUND INFORMATION

It is known that a key element for achieving laboratory-grade precision and accuracy is the use of an aqueous-based calibration solution containing known concentrations of all analytes to be tested. Typically, a single point calibration is performed immediately prior to the measurement of a clinical sample. This ensures reproducible results from instrument-to-instrument and from sensor-to-sensor. The current sensor or "optode" cassettes used in certain optical sensor based instruments, such as OPTI® instruments of Osmetech® (Roswell, Ga.), are wet-stored in the calibration solution, thus no waiting period is needed for sensors to wet-up from the dry state prior to use. The principal disadvantage for wet-storage is the resulting sensor "shelf-life" limitation, especially for certain sensors such as biosensors with hydrolytically unstable components. In addition, a requirement of being able to store wet calibration solution significantly complicates cassette design, thus increasing costs.

SUMMARY OF THE INVENTION

To circumvent these and other disadvantages, a new sensor architecture is provided that allows single-use, disposable cassettes, which contain dry-stored and dry-calibrated fluorescence sensors, to be used in a variety of ambient conditions for the measurement of various analyte concentrations in a variety of samples, including but not limited to biological fluid samples or samples taken from the environment.

The invention utilizes one or more fluorescence optical sensors to measure the intensity of light emitted from fluorescent dyes exposed to a specific analyte. The principle of measurement is similar to that used in wet-calibrated optical sensors. The concentration of the analyte is determined from the observed "dry" fluorescence intensity signal ($I_{dry}$) and that observed with a sample in place containing an unknown concentration of analyte ($I_{unknown}$). The dry calibration process is based on a simple well-defined ratio of fluorescence intensity in a sensor's dry state ($I_{dry}$, which is the same for sensors within each manufactured lot) to that in the sensor's mid-physiologic wet state, that is, the fluorescence intensity at known mid-physiologic analyte levels ($I_{known}$). This dry-to-wet (mid-physiologic) relationship is stable and consistent for all sensors in a lot and is characterized and bar-coded at a factory. In addition, the sensor's wet response curve of the fluorescence intensity versus varying analyte level is also factory-characterized and bar-coded, similar to the proven method employed in a wet-calibrated sensor. In other words, if one assumes that a sensor's response to varying concentration levels of analyte is linear, then one can plot ($I_{known}/I_{dry}$) or "x" against the known concentrations of analyte or "y" to arrive at a straight line with slope m and intercept b. Using the well known equation y=mx+b, one can determine the concentration of analyte in a sample, y, if one can measure x, which is the ratio of intensities ($I_{unknown}/I_{dry}$).

During sample measurement at a user's site, the sensor's dry fluorescence intensity ($I_{dry}$) and the sensor's wet fluorescence intensity after making contact with an aqueous sample ($I_{unknown}$) are measured. The concentration of analyte present in the sample is then computed from the ratio of the observed fluorescence intensities ($I_{unknown}/I_{dry}$) using the dry-to-wet relationship of sensor fluorescence intensity responses that is established at a factory for that particular lot of sensors. The sensors' response to varying concentrations of analyte may not always be linear, of course. Whatever the case, an appropriate mathematical relationship is utilized to arrive at the calculated analyte concentration for a sample.

In the present invention, all sensor elements are coated onto a suitable support material (more below). The sensor itself may be comprised of one or more layers designed to achieve a specific function (analyte recognition, buffering, filtering, etc.). The sensors are then desiccated using suitable drying media such as molecular sieves, silica gel, etc. Under consistent desiccation conditions, the sensors achieve a standardized and reproducible calibration point.

Moreover, by making use of a ratio of dry and wet sample responses rather than an absolute sensor response, the present method accommodates minor variations in sensor preparation, as well as instrument-related variability. This approach is also advantageous because the calibration point is consistently accomplished, as described above, by suitable choice of desiccant material. A consistent choice of desiccant helps to ensure that the only variable is the analyte concentration in the sample.

This invention aims to overcome two major issues in developing ion sensors. One embodiment is to create a spreading layer on the top surface of the sensor architecture (see, FIG. 1) to effectively spread various biological samples including those from various animal species, which inherently spread only with difficulty. Another embodiment of the invention is to create a humidity control layer that works within a one embodiment of the sensor architecture (again, FIG. 1) to selectively control the transport of moisture/water through the humidity control layer, thus eliminating the bias of sensor responses measured at different humidity environments.

Thus the present invention provides a humidity control layer having opposing sides, the layer effective to inhibit undesirable effects of varying levels of humidity present on one side of the layer, comprising: (a) a water-insoluble, porous matrix, including a plurality of channels or through holes at least some of which extend from one side of the layer to an opposing side; and (b) one or more water-soluble, solid, polymeric substances that fill a substantial portion of the plurality of channels or through holes. In some embodiments the humidity control layer has a dry thickness ranging from about 20 μm to about 100 μm, for instance, about 50 μm. In one embodiment of the invention, the matrix is comprised of a cellulose, poly(styrene-divinylbenzene) copolymer, D4 hydrogel, D6 hydrogel, poly(acrylonitrile)-co-poly(acrylamide), cross-linked poly(vinyl alcohol), or combinations thereof, whereas the one or more polymeric substances comprise poly(vinyl pyrrolidone), hydroxyethylcellulose, hydroxypropylcellulose, carboxymethylcellulose, maltodextrin, or combinations thereof. It has been found that the one or more polymeric substances ideally have an average molecular weight ranging from about 800,000 to about 2,000,000 Daltons, for example, ranging from about 1,100,000 to about 1,500,000 Daltons, such as an average molecular weight of about 1,300,000 Daltons.

The humidity control layer is typically prepared by casting a solution comprising the recited components dissolved in a suitable, solubilizing solvent and allowing the cast solution to dry. In some embodiments, the viscosity of a solution comprising an ethanol-water solvent mixture and the components (a) and (b) of the layer described above ranges from about 600 to about 3000 cps.

The present invention also provides a spreading layer having opposing surfaces, the layer effective to promote a desirable rate of spreading of a liquid sample applied on one surface of the layer, comprising: (a) a water-insoluble, porous matrix, including a plurality of channels or through holes at least some of which extend from one surface to an opposing surface, the matrix further characterized as including fibers having a length falling in the range of about 50 μm to about 400 μm; (b) one or more water-soluble, solid, polymeric substances that fill a substantial portion of the plurality of channels or through holes; and (c) one or more hydrophilic, super absorbent materials. In one embodiment of the invention the spreading layer has a dry thickness ranging from about 80 μm to about 150 μm, for example, about 120 μm. In another embodiment of the invention the matrix component of the spreading layer is comprised of a cellulose, poly(styrene-divinylbenzene) copolymer, D4 hydrogel, D6 hydrogel, poly(acrylonitrile)-co-poly(acrylamide), cross-linked poly(vinyl alcohol), or combinations thereof.

In one embodiment of the invention the matrix comprises a fibrous support matrix, in which the fibers of the support matrix have a length falling in the range of about 50 μm to about 400 μm, for example, about 200 μm to about 300 μm, such as about 250 μm.

On the other hand, the one or more polymeric substances comprise poly(vinyl pyrrolidone), hydroxyethylcellulose, hydroxypropylcellulose, carboxymethylcellulose, maltodextrin, or combinations thereof. Furthermore the one or more polymeric substances may have an average molecular weight ranging from about 500,000 to about 5,000,000 Daltons, for example, ranging from about 800,000 to about 1,200,000 Daltons.

A suitable spreading layer will possess one or more super absorbent materials, which may comprise poly(acrylic acids), poly(acrylic amides), their salts, or combinations thereof. As discussed further herein, the pH value of a solution comprising an ethanol-water solvent mixture and the components (a), (b), and (c) of the spreading layer recited above ideally ranges from about 7.4 to about 10, certainly no more than about 12.

The invention also provides a multi-layered laminate comprising in ascending vertical sequence: (i) an indicator layer, (ii) an overcoat layer, (iii) a humidity control layer, (iv) a sample loading layer, and (v) a spreading layer. In one embodiment of the invention an indicator layer comprises an indicator sensitive to the presence of sodium ion, chloride ion, or potassium ion. An indicator layer according to the invention may have a dry thickness ranging from about 5 μm to about 20 μm. An overcoat layer according to the invention comprises a substance that blocks visible light (e.g., carbon black). An overcoat layer may have a dry thickness ranging from about 5 μm to about 20 μm. Consistent with the objectives of the invention a sample loading layer having opposing sides is provided and comprises a water-insoluble, porous matrix, including a plurality of channels or through holes at least some of which extend from one side of the layer to an opposing side. The sample loading layer may comprise in one embodiment of the invention a combination of a cellulosic material and a hydrogel.

In one embodiment of the invention the laminate is one in which each layer in the ascending vertical sequence includes at least one chemical component that is also present in an adjacent layer. For instance, the humidity control layer includes a first chemical component that is also present in the adjacent overcoat layer and a second chemical component that is also present in the adjacent sample loading layer.

A process of preparing a multi-layered laminate is also described. The steps of the process comprises casting a first solution to form an indicator layer, casting a second solution over the indicator layer to form an overcoat layer, casting a third solution over the overcoat layer to form a humidity control layer, casting a fourth solution over the humidity control layer to form a sample loading layer, and casting a fifth solution over the sample loading layer to form a spreading layer. For example, the process of the invention includes a step in which the solution used to form each layer is allowed to dry or evaporate after being cast.

Other processes, methods, and articles of manufacture are also evident from the description of the invention. For example, a method is provided of inhibiting undesirable effects of varying levels of humidity on an indicator layer, whose response is sensitive to varying levels of humidity, which method comprises establishing a humidity control layer over a surface of the indicator layer, which surface is susceptible to exposure to varying levels of humidity, the humidity control layer having a composition and thickness, which are effective to inhibit undesirable effects of varying levels of humidity.

Another method provided is a method of promoting a desirable rate of spreading of a liquid sample comprising contacting the liquid sample with a spreading layer having a composition and thickness, which are effective to promote a desirable rate of spreading of the liquid sample.

Another article of the invention includes spreading layer having opposing surfaces, the layer effective to promote a desirable rate of spreading of a liquid sample applied on one surface of the layer. Such an article comprises: (a) a means for providing a layer having a plurality of channels or through holes at least some of which extend from one surface of the layer to an opposing surface of the layer; (b) a means for filling a substantial portion of the plurality of channels or through holes; and (c) a means for promoting absorption of a liquid sample applied on one surface of the layer. In one embodiment of the invention, the means for providing the layer of interest further includes providing fibers having a predetermined average length. For example, the predetermined average length of such fibers ranges from about 50 μm to about 400 μm.

Other embodiments and processes, including alternative components and substances, will be evident to those of ordinary skill in the art based on the detailed descriptions provided herein.

DETAILED DESCRIPTION OF THE INVENTION

Figure 1:
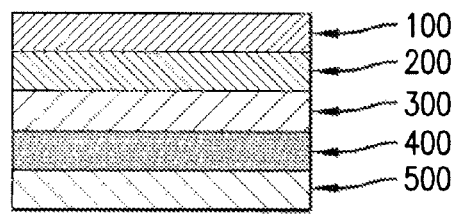
FIG. 1 shows a cross-sectional view of one embodiment of an analyte detection sensor in accordance with the present invention. Element 100 designates a Spreading layer, element 200 designates a Sample Loading layer, element 300 designates a Humidity Control layer, element 400 designates an Overcoat layer, and element 500 designates an Indicator layer.

The sensor of the present invention comprises an indicator layer containing ionophore/fluorophore sensing molecules (Element 500, FIG. 1). A change in an analyte concentration will cause a change in intensity of a fluorescence signal, thus allowing analyte concentration to be determined. In one embodiment, cellulosic particles having an average size ranging from about 2-25 μm, such as 2-20 μm (or, for instance, having an average particle size of about 10 μm) are included in the indicator layer.

Furthermore, the sensor architecture is also comprised of an overcoat layer containing carbon black for optical isolation (Element 400, FIG. 1) dispersed, for example, in a water-insoluble hydrogel.

Figure 2:
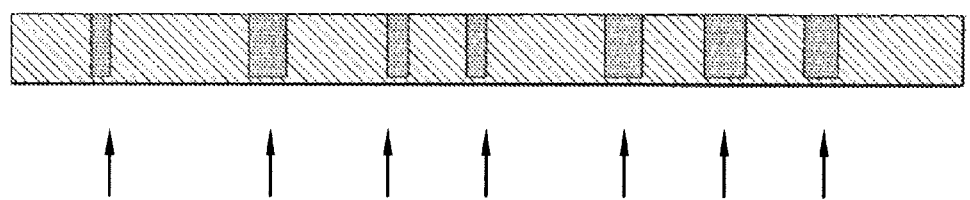
FIG. 2 is a cross-sectional depiction of element 300, a Humidity Control layer, to illustrate the notion of the presence of many channels or through holes within this layer, which includes a water-insoluble, porous matrix, such as a cellulosic material or a suitable hydrogel. The channels or through holes are filled with one or more solid, high-molecular-weight, hydrophilic, water-soluble substances, which are indicated by the arrows.

Furthermore, the sensor architecture is also comprised of a humidity control layer (Element 300, FIG. 1). In one embodiment, cellulosic particles having an average particle size ranging from about 7-20 μm are included in the humidity control layer. There are many channels or through holes inside this layer, which includes a water-insoluble, porous matrix. These channels or through holes are filled with one or more solid, high molecular weight, hydrophilic, water-soluble substances (see, FIG. 2). The water/moisture cannot reach the underlying indicator layer until the filling material is dissolved, which typically happens only when the sample (typically an aqueous liquid) comes into contact with the sensor. Thus by controlling the solubility of the filling material and the thickness of the layer, the transport of the water/moisture can be controlled reliably, thus eliminating unwanted effects of environment humidity on sensor responses at least within the time period of an analytical test, which can last from about 1 minute to several minutes (e.g., 10-12 minutes). Typically, a sensor cartridge is removed from its sealed package, placed in the appropriate compartment of a table top analytical instrument (e.g., OPTI® LION and associated OPTI® LION cassettes), dry fluorescence intensity signal measured, sample applied, and wet fluorescence intensity signal measured—all typically within about 1 and about 10 minutes.

Furthermore, in one embodiment, the sensor architecture is also comprised of a sample loading layer (Element 200, FIG. 1). This layer may be comprised of cellulosic particles having an average particle size ranging from about 7-20 μm and hydrophilic polymer (e.g., a hydrogel); thus sample loading layer is porous and hydrophilic in nature. The sample loading layer helps present a more uniform layer of sample against the humidity control layer.

Still more, the present invention is comprised a spreading layer (Element 100, FIG. 1), in which long fiber particles (e.g., ranging in average length of about 50 μm to about 400 μm, for example about 200-300 μm in average length; while the preceding ranges of average lengths are typical, it should be apparent that individual fibers comprising the spreading layer can have a broad range of individual lengths beyond even the exemplary range of about 50 μm to about 400 μm) and high molecular weight, hydrophilic, super-absorbent substances are incorporated to improve the spreading of biological samples. This spreading layer helps to eliminate, if not prevent, the spreading variation observed with different biological samples and with different sample volumes. It should be understood that in the case of cellulosic materials, a smaller size provides more particle-like materials whereas a larger size implies more fibrous-like materials.

In accordance with the invention, a combination of layers, each serving multiple/different functions, is provided. Moreover, it has been discovered that the transport of a substance through a membrane (or layer) can be modulated by controlling the solubility of the transported substance in a "filling" material, which is also present within the inner channels of the membrane (or layer). Each layer in the combination is different from one another in that each layer is composed of a different combination of chemical substances. Yet it has been discovered that if there is at least one chemical substance that exists in common between the combined components of adjacent layers, an enhancement in desirable adhesion between adjacent layers is surprisingly observed, making for a better, more durable laminate. What is more, the inventors have shown that the pH value of the spreading layer can be changed, thus optimizing and achieving effective spreading. The results of such experiments involving changes in pH are described in further detail, below. It has also been observed that the fiber length of the support matrix of the spreading layer can be changed, thus optimizing and achieving effective spreading.

Humidity Barrier:

In order to accomplish the desired humidity protection, the hydrophilic material in the humidity barrier should ideally take up moisture at a low rate. A suitable humidity control layer may be comprised, for example, of a water-insoluble, support matrix, including cellulose particles, D4 and/or D6 hydrogel (available from CardioTech International, Woburn, Mass.) and a water-soluble, solid, polymeric substance, such as PVP and the like, as a filler. Examples of some suitable materials that can make up supporting matrices include, but are not limited to, cellulose, poly(styrene-co-divinylbenzene) copolymer (PS), D4 and/or D6 hydrogel, poly(acrylonitrile)- co-poly(acrylamide), and cross-linked poly(vinyl alcohol), all available from Aldrich, Saint Louis, Mo. Examples of some suitable filler materials include, but are not limited to, poly(vinyl pyrrolidone) (PVP), hydroxyethylcellulose (HEC), hydroxypropylcellulose (HPC), carboxymethylcellulose (CMC), all available from Aldrich, Saint Louis, Mo. and maltodextrin (Grain processing corporation, Muscatine, Iowa).

The extent of moisture uptake is controlled by careful choice of the average molecular weight (MW) of the hydrophilic material. Typical average molecular weights range from about 800,000 Daltons to 2,000,000 Daltons, such as about 1.1 million to about 1.5 million Daltons, or about 1.2 million to about 1.4 million Daltons. The inventors have discovered that a MW of about 1.3 million Daltons appears to work very well.

Additional consideration is given to the "coatability" of the material, which is achieved by controlling the viscosity of the humidity barrier solution used to prepare a layer of the humidity barrier. Typical viscosities of the humidity barrier solution range from about 600 to about 3000 cps, for instance from about 1000 cps to about 1900 cps or a value of around 1500 cps.

Sample Spreading Layer:

Rapid absorption of biological samples is accomplished by using hydrophilic, super absorbent materials. Examples of such materials include, but are not limited to, polyacrylates (PAA), polyacrylamides and the like. The molecular weight range for these polymers ranges for instance from about 500,000 to about 5,000,000 Daltons, such as from about 800,000 Daltons to about 1.2 million Daltons. An exemplary value of molecular weight is about 1 million Daltons. In addition, the counter-ion used in the super absorbent material must not interfere with the sensor. Typical non-interfering counter-ions include, but are not limited to, tetramethyl ammonium, tetraethyl ammonium and tetrabutyl ammonium ions, with tetramethyl ammonium ion being a exemplary counter-ion.

The pH value of the sample spreading layer is important to ensure rapid sample absorption, because the super hydrophilicity of PAA comes from its salt, instead of free acid. In order to maintain sufficient hydrophilicity, a certain degree of carboxylic acid on the PAA chain has to be deprotonated to form some charged species, namely, carboxylate and its counter ion. The degree of deprotonation of carboxylic acid of PAA depends on the final pH value of the solution used to prepare the dispersion. Theoretically, and not wishing to be limited by theory, PAA shows better hydrophilicity at higher pH value. But too high a pH value will facilitate the decomposition of the matrix and ion indicator. Specifically, the solution used to prepare the spreading layer should have a pH value of about 7.4 or greater. For example, the pH value is about 8.1. An illustrative pH value does not exceed about 10.

Furthermore, a fibrous support such as fibrous cellulose helps to spread the sample rapidly over the sensor surface. It has been discovered that the fiber length of the cellulose is very important, if not critical, to achieving rapid spreading. Typically, the average fiber lengths may vary from about 50 to about 400 micrometers, such as from about 200 micrometers to about 300 micrometers. A very suitable average fiber length appears to be about 250 micrometers.

Multi-Layered Laminates:

Example 1

One embodiment of the present invention, a sodium sensor, is described as follows. Such sensors are prepared as described further below.

0.5 g cellulose powder (25 µm sieved) with immobilized indicator (U.S. Pat. No. 5,952,491, the entire disclosure of which is incorporated by reference herein) was suspended in 9.5 g 10% (w/w) D4 hydrogel in 90% (w/w) ethanol-water for 16 h. The resulting homogeneous dispersion was coated onto a polyester foil (8.5"×11" sheet) to a final dry thickness of 10 µm to form the Indicator layer as shown in FIG. 1. The Indicator layer was then coated with a dispersion consisting of 0.3 g carbon black suspended in 9.7 g 10% (w/w) D4 hydrogel in 90% (w/w) ethanol-water to a dry thickness of 5 µm to form an Overcoat layer. The Overcoat layer was then coated with a Humidity Control layer containing 0.5 g cellulose (10 µm), 1.0 g PVP and 8.5 g 10% (w/w) D4 hydrogel in 90% (w/w) ethanol-water to a dry thickness of 50 µm. The Humidity Control layer was then coated with an Sample Loading layer containing 0.5 g cellulose (20 µm) and 9.5 g 10% (w/w) D4 hydrogel in 90% (w/w) ethanol-water to a dry thickness of 10 µm. Finally, the Sample Loading layer was coated with a Spreading layer containing 0.0075 g polyacrylic acid (PAA), 0.2 g PVP and 1.0 g cellulose (250 µm) in 8.8 g 50% (w/w) ethanol-water (the pH value of this dispersion was adjusted to 8.0 using 10% (w/w) tetramethylammonium hydroxide in water) to a final thickness of 100 µm.

Example 2

One embodiment for an optical chloride sensor, according to the present invention, is prepared as described below.

1.5 g of immobilized chloride indicator (U.S. Pat. No. 6,613,282, the entire disclosure of which is incorporated by reference herein) was suspended in 8.5 g of 10% (w/w) D4 hydrogel in 90% (w/w) ethanol-water for 16 h. The resulting homogeneous dispersion was coated onto a polyester film (8.5"×11" sheet) to a final dry thickness of 10 µm to form the Indicator layer as shown in FIG. 1. The Indicator layer was then coated with 0.3 g carbon black suspended in 9.7 g 10% (w/w) D4 hydrogel in 90% (w/w) ethanol-water to a dry thickness of 5 µm to form an Overcoat layer. The Overcoat layer was then coated with a solution containing 0.3 g cellulose (15 µm), 0.5 g polyvinyl pyrrolidone (PVP) and 9.2 g 10% (w/w) D4 hydrogel in 90% (w/w) ethanol-water to a dry thickness of 20 µm to form the Humidity Control layer. The Humidity Control layer was then coated with a solution containing 0.3 cellulose (15 µm) and 9.7 g 10% (w/w) D4 hydrogel in 90% (w/w) ethanol-water to a dry thickness of 10 µm to form a Sample Loading layer. Finally, the Sample Loading layer was coated with a solution containing 0.005 g polyacrylic acid (PAA), 0.2 g PVP and 1.0 g cellulose (200 µm) in 8.8 g 50% (w/w) ethanol-water (the pH value of this dispersion was adjusted to 8.0 using 10% (w/w) tetramethylammonium hydroxide in water) to a final thickness of 120 µm to form the Spreading layer.

Example 3

One embodiment for an optical potassium sensor, according to the present invention, is prepared in the manner described further below.

0.5 g cellulose powder (10 µm sieved) with immobilized potassium indicator (U.S. Pat. No. 6,211,359, the entire disclosure of which is incorporated by reference herein) was suspended in 9.5 g of 10% (w/w) D4 hydrogel in 90% (w/w) ethanol-water for 16 h. The resulting homogeneous dispersion was coated onto a polyester film (8.5"×11" sheet) to a final dry thickness of 10 µm to form the Indicator layer as shown in FIG. 1. The indicator layer was then coated with 0.3 g carbon black suspended in 9.7 g 10% (w/w) D4 hydrogel in 90% (w/w) ethanol-water to a dry thickness of 5 μm to form an Overcoat layer. The overcoat layer was then coated with a solution containing 0.7 g cellulose (20 μm), 1.5 g polyvinyl pyrrolidone (PVP) in 7.8 g 10% (w/w) D4 hydrogel in 90% (w/w) ethanol-water to a dry thickness of 40 μm to form the Humidity Control layer. The Humidity Control layer was then coated with a solution containing 0.7 g cellulose (10 μm) in 9.3 g 10% (w/w) D4 hydrogel in 90% (w/w) ethanol-water to a dry thickness of 20 μm to form a Sample Loading layer. Finally, the Sample Loading layer was coated with a solution containing 0.005 g polyacrylic acid (PAA), 0.2 g PVP and 1.0 g cellulose (300 μm) in 8.8 g 50% (w/w) ethanol-water (the pH value of this dispersion was adjusted to 8.0 using 10% (w/w) tetramethylammonium hydroxide in water) to a final thickness of 100 μm to form the Spreading layer.

Representative Results

Figure 3A:
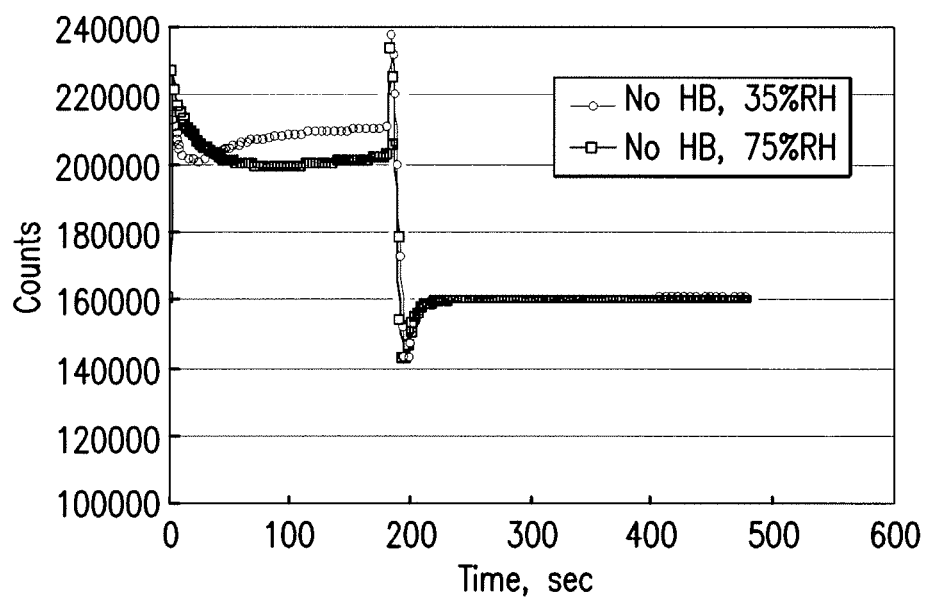
FIG. 3A shows the performance of sodium sensors prepared without a Humidity Control layer. The results can be compared with sodium sensors coated with a Humidity Control layer (FIG. 3B). The sensors' responses were compared after exposing the sensors to different levels of humidity (35% RH & 75% RH) over a period of approximately 2 minutes.
Figure 3B:
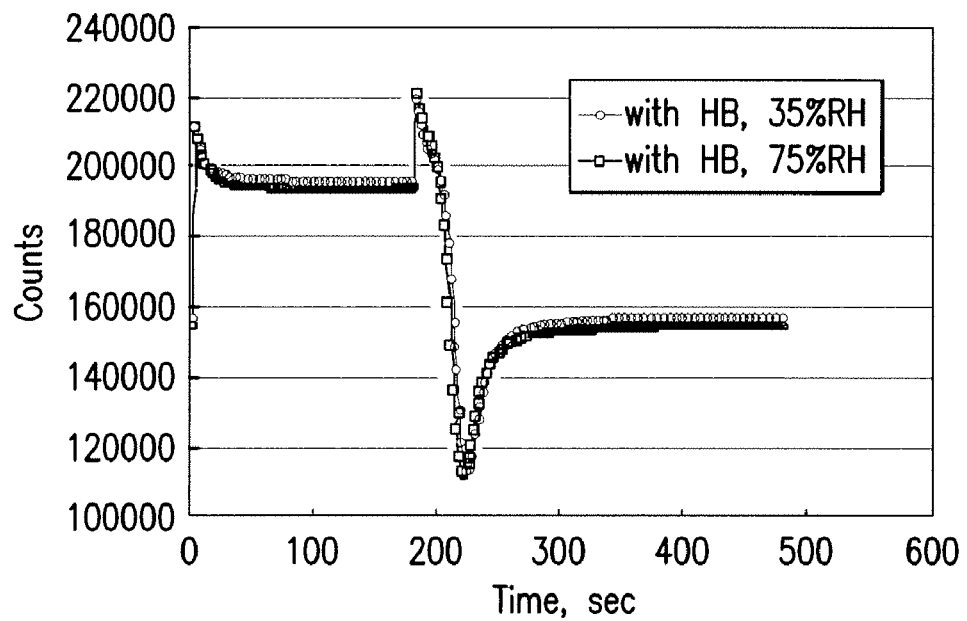
Figure 4:
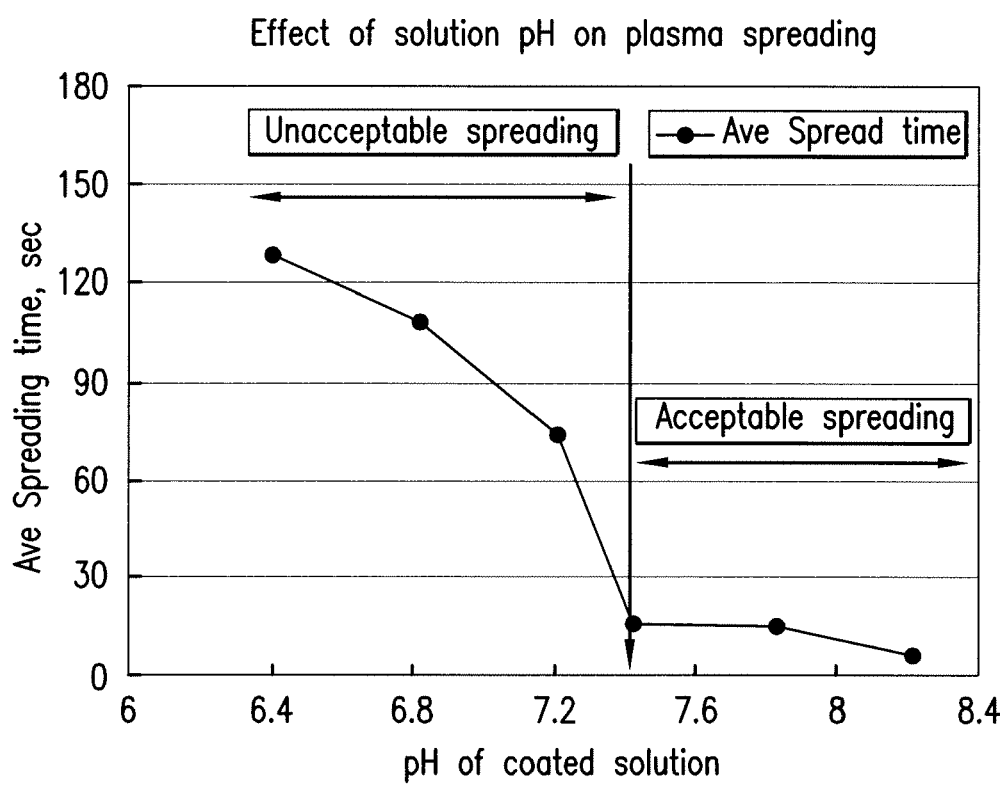
FIG. 4 shows the effect of the pH level of the Spreading layer solution on the sample spreading time for a 7 μL volume of a feline plasma sample applied on a sensor surface.

FIG. 3A shows the performance of sodium sensors prepared without the humidity control layer compared with those sensors that were coated with the humidity control layer (FIG. 3B). The responses were compared after exposing the sensors to different humidities (35% RH & 75% RH) for 2 minutes. It is evident from the results that a more consistent response is obtained when laminates include a humidity control layer or barrier of the invention.

TABLE 1

Summary of the effect that the varying humidity levels impose on the sensor response variation with and without the presence of a Humidity Control layer (Humidity barrier).

| | Variation in response 35% RH vs. 75% RH |
|---|---|
| Sensor without Humidity barrier | 3.86% |
| Sensor with Humidity barrier | 0.44% |

TABLE 2

Summary of the average spreading time of Spreading layers prepared with solutions at different pH levels.

| Final pH | Ave Spread time, sec |
|---|---|
| 6.4 | 128 |
| 6.82 | 108 |
| 7.21 | 73 |
| 7.43 | 16 |
| 7.83 | 15 |
| 8.21 | 6 |

What is claimed is:

1. A multi-layered laminate comprising in ascending vertical sequence: (i) an indicator layer, (ii) an overcoat layer, (iii) a humidity control layer, (iv) a sample loading layer, and (v) a spreading layer, wherein
the humidity control layer (iii) has opposing sides, the layer effective to inhibit undesirable effects of varying levels of humidity present on one side of the layer, comprising:
   (a) a water-insoluble, porous matrix, including a plurality of channels or through holes at least some of which extend from one side of the layer to an opposing side; and
   (b) one or more water-soluble, solid, polymeric substances that fill a substantial portion of the plurality of channels or through holes; and
the spreading layer (v) has opposing surfaces, the layer effective to promote a desirable rate of spreading of a liquid sample applied on one surface of the layer, comprising:
   (a') a water-insoluble, porous matrix, including a plurality of channels or through holes at least some of which extend from one surface to an opposing surface, the matrix further characterized as including fibers having an average length falling in the range of about 50 μm to about 400 μm;
   (b') one or more water-soluble, solid, polymeric substances that fill a substantial portion of the plurality of channels or through holes; and
   (c') one or more hydrophilic, super absorbent materials.

2. The laminate of claim 1 in which the indicator layer comprises an indicator sensitive to the presence of sodium ion.

3. The laminate of claim 1 in which the indicator layer comprises an indicator sensitive to the presence of chloride ion.

4. The laminate of claim 1 in which the indicator layer comprises an indicator sensitive to the presence of potassium ion.

5. The laminate of claim 1 in which the indicator layer has a dry thickness ranging from about 5 μm to about 20 μm.

6. The laminate of claim 1 in which the overcoat layer comprises a substance that blocks visible light.

7. The laminate of claim 6 in which the overcoat layer has a dry thickness ranging from about 5 μm to about 20 μm.

8. The laminate of claim 1 in which the sample loading layer has opposing sides and comprises a water-insoluble, porous matrix, including a plurality of channels or through holes at least some of which extend from one side of the layer to an opposing side.

9. The laminate of claim 1 in which each layer in the ascending vertical sequence includes at least one chemical component that is also present in an adjacent layer.

10. The laminate of claim 1 in which the humidity control layer includes a first chemical component that is also present in the adjacent overcoat layer and a second chemical component that is also present in the adjacent sample loading layer.

11. A process of preparing the multi-layered laminate according to claim 1 comprising: casting a first solution to form the indicator layer, casting a second solution over the indicator layer to form the overcoat layer, casting a third solution over the overcoat layer to form the humidity control layer, casting a fourth solution over the humidity control layer to form the sample loading layer, and casting a fifth solution over the sample loading layer to form the spreading layer.

12. The process of claim 11 in which the solution used to form each layer is allowed to dry or evaporate after being cast.

* * * * *